United States Patent [19]

Tatarintsev

[11] Patent Number: 5,932,621
[45] Date of Patent: Aug. 3, 1999

[54] METHODS OF USING AJOENE FOR THE TREATMENT OF TUMORS

[75] Inventor: Alexander V. Tatarintsev, Moscow, Russian Federation

[73] Assignee: John B. Davidson, Chicago, Ill.

[21] Appl. No.: 08/444,970

[22] Filed: May 19, 1995

Related U.S. Application Data

[62] Division of application No. 07/906,850, Jun. 30, 1992, abandoned.

[51] Int. Cl.$^6$ .................... A61K 31/105; A61K 31/10
[52] U.S. Cl. .............................. 514/707; 514/708
[58] Field of Search .................... 514/707, 708

[56] References Cited

U.S. PATENT DOCUMENTS

| | | | |
|---|---|---|---|
| 4,126,676 | 11/1978 | Sanders | 424/98 |
| 4,341,762 | 7/1982 | Haast | 424/88 |
| 4,643,994 | 2/1987 | Block et al. | |
| 4,665,088 | 5/1987 | Apitz-Castro et al. | |
| 4,876,281 | 10/1989 | Yoshida et al. | 514/517 |
| 5,066,658 | 11/1991 | Demers et al. | 514/707 |
| 5,093,122 | 3/1992 | Kodera | 424/195.1 |
| 5,380,646 | 1/1995 | Knight et al. | 424/1.69 |
| 5,464,855 | 11/1995 | Capiris et al. | 514/382 |

FOREIGN PATENT DOCUMENTS

| | | |
|---|---|---|
| 153881 | 9/1985 | European Pat. Off. . |
| 185324 | 6/1986 | European Pat. Off. . |
| WO 94/15953 | 7/1994 | WIPO . |

OTHER PUBLICATIONS

Sud'ina et al., 1991, *Biochimica et Biophysica Acta*, 1091:257–60.
Tatarintsev et al., International Conference on Molec. Biol. Aspects of Diagnostics and Therapy of AIDS, Conference poster and abstract, Jul. 2–5, 1991.
Tatarintsev et al., European Developmental Biology Congress, Conference abstract, Aug. 11–15, 1991.
Tatarintsev et al., Keystone Symposia on Molec. & Cell. Biol., Conference abstract, Feb. 1992.
Tatarintsev et al., Keystone Symposia on Molec. & Cell. Biol., Conference abstract, Mar. 1992.
Karamov et al., Keystone Symposia on Molec. & Cell. Biol., Conference Abstract, Apr. 4, 1992.
Tatarintsev et al., Keystone Symposia on Molec. & Cell. Biol., Conference abstract, Apr. 4, 1992.
Tatarintsev et al., VIII Int'l Conf. on AIDS, Conference abstract, Jul. 19–24, 1992.
Apitz–Castro et al., 1983, *Thrombosis Research*, 32(2):155–69.
Block et al., 1984, *J. Am. Chem. Soc.*, 106(26):8295–96.
Block et al., 1986, *J. Am. Chem. Soc.*, 108(22):7045–55.
Apitz–Castro et al., 1986, *Thrombosis Research*, 42:303–11.
Apitz–Castro et al., 1986, *Biochemical and Biophysical Research Communications*, 141(1):145–50.
Jain et al., 1987, *TIBS*, 12(7):252–54.
Jamaluddin et al., 1988, *Biochemical and Biophysical Research Communications*, 153(1):479–86.
Apitz–Castro et al., 1988, *Drug Research*, 38(7):901–04.
Debouzy et al., 1989, *European Biophysics Journal*, 17:211–16.
Rendu et al., 1989, *Biochemical Pharmacology*, 38(8):1321–28.
Apitz–Castro et al., 1991, *Biochemica et Biophysica Acta*, 1094(3):269–80.
Apitz–Castro et al., 1991, *Thrombosis and Haemotology*, 65(6):Abstract No. 1380 at p. 1079.
Apitz–Castro et al., 1991, *Thrombosis and Haemotology*, 65(6):Abstract No. 1603 at p. 1141.
Srivestava, 4th Erfurt Conference on Platelets, Jun. 22–27, 1992, p. 19.
Ali et al., Book of Abstracts, VIII Int'l Conf. on Prostaglandins & Related Compounds, Montreal, Jul. 1992, abstract No. 54.
Apitz–Castro et al., *Platelet Membrane I*, No. P1077, 1987.
Apitz–Castro et al., *Platelet Pharmacology III*, No. 0747, 1988.
Apitz–Castro et al., Supplementary Abstracts, No. 2021, 1990.
Belman et al., 1989, *Journal of Biochemical Toxicology*, 4(3):151–60.
Scharfenberg et al., 1990, *Cancer Letters*, 53:103–08.
Yoshida et al., 1987, *Applied and Environmental Microbiology*, 53(3):615–17.
San–Blas et al., 1989, *Antimicrobial Agents and Chemotherapy*, 33(9):1641–44.
Singh et al., 1990, *Can. J. Bot.*, 68(6):1354–56.
Gargouri et al., 1989, *Biochemica et Biophysica Acta*, 1006(1):137–39.
Mohammed et al., 1986, *Thrombosis Research*, 44:793–806.
Mayeux et al., 1986, *Prostaglandins 1*, 45(3):Abstract 2936 at p. 660.
Mayeux et al., 1988, *Agents and Actions*, 25:182–90.
Tang et al., *Chinese Drugs of Plant Origin: Chemistry, Pharmacology, and Use in Traditional and Modern Medicine*, Chapter 11, 1991.
Mirelman et al., 1987, *The Journal of Infectious Diseases*, 156(1):243–44.
Chowdhury et al., 1991, *Indian Journal of Medical Research*, [A]93:33–36.
Shalinsky et al., 1989, *Prostaglandins*, 37(1):135–48.
Focke et al., 1990, *FEBS Letters*, 261(1):106–08.
Kourounakis et al., 1991, *Research Communications in Chemical Pathology and Pharmacology*, 74(2):249–52.
Liakopoulou–Kyriakides et al., 1985, *Phytochemistry*, 24(3):600–01.
Liakopoulou–Kyriakides, 1985, *Phytochemistry*, 24(7):1593–94.

(List continued on next page.)

*Primary Examiner*—William R. A. Jarvis
*Attorney, Agent, or Firm*—Sheridan Ross P.C.

[57] ABSTRACT

The present invention relates to the use of Ajoene to treat integrin-mediated tumors and metastasis.

11 Claims, 1 Drawing Sheet

OTHER PUBLICATIONS

Nagai, 1973, *Japanese Journal of Infectious Diseases,* 47:321–25.
Bordia, 1978, *Athersclerosis,* 30:355–60.
Esanu, 1981, *Rev. Roum. Med.–Virol.,* 32(1):57–77.
Tsai et al., 1986, *Chemical Abstracts,* 104(24):No. 61572a.
Bayer et al., 1988, *Planta Medica,* 54(6):560 K1–6.
Block, 1985, *Scientific American,* 252(3):94–99.
Auger et al., 1990, *Chemosphere,* 21(7):837–43.
Jansen et al., 1987, *Planta Medica,* 53(6):559–62.
Yu et al., 1989, *Journal of Food Science,* 54(4):977–81.
Saito et al., 1989, *Journal of the Association of Analytical Chemists,* 72(6):917–20.
Ziegler et al., 1987, *Pharmaceutisch Weekblad Scientific Edition,* 9(4):248 (Abstract).
Mochizuki et al., 1988, *Journal of Chromatography,* 455:271–77.
Lancaster et al., 1989, *Phytochemistry,* 28(2):455–60.
Lancaster et al., 1989, *Phytochemistry,* 28(2):461–64.
Ziegler et al., 1989, *Journal of Liquid Chromatography,* 12(1 & 2):199–200.
Ziegler et al., 1989, *Planta Medica,* 55(4):372–78.
Nock et al., 1986, *Archives of Biochemistry and Biophysics,* 249(1):27–33.
Nock et al., 1987, *Plant Physiology,* 85(4):1079–83.
Knobloch et al., 1987, *Pharmaceutisch Weekblad Scientific Edition,* 9:218.
Knobloch et al., 1988, *Planta Medica,* 54(6):561–62, K1–9.
Jansen et al., 1989, *Planta Medica,* 55:434–49.
Jansen et al., 1989, *Planta Medica,* 55:440–45.
Nock et al., 1989, *Phytochemistry,* 28(3):729–31.
Won et al., 1989, *Physiologia Plantarum,* 77(1):87–92.
Fugita et al., 1990, *Arch. of Biol. & Chem.,* 54(4):1077–79.
Rabinkov et al., 1991, *Mechanisms of Action III,* 5:1149 Abstract No. 4509.
Gmelin et al., 1976, *Phytochemistry,* 15(11):1717–21.
Ibert et al., 1990, *Planta Medica,* 56(2):202–11.
Ibert et al., 1990, *Planta Medica,* 56(3):320–26.
Lawson et al., 1991, *Planta Medica,* 57(3):263–70.
Sendl et al., 1991, *Planta Medica,* 57(4):361–62.
Lawson et al., 1991, *Planta Medica,* 57(4):363–70.
Blania et al., 1991, *Planta Medica,* 57:(4):371–75.
Yu et al., 1989, *Journal of Agric. Food Chem.,* 37(3):725–30.
Yu et al., 1989, *Journal of Agric. Food Chem.,* 37(3):730–34.
Yu et al., 1989, *Journal of Food Science,* 54(3):632–35.
Yu et al., 1989, *Journal of Chromatography,* 462:137–45.
Lawson et al., 1991, *Journal of Natural Products,* 54(2):436–44.
Phillips et al., 1988, *Blood,* 71:831–43.
Barbillari et al., 1993, *Proc. Natl. Acad. Sci. USA,* 90:7941.
Blood et al., 1990, *Biochim. Biophys. Acta,* 1032:89–118.
Brake et al., 1990, *J. Cell Biol.,* 111:1275.
Cheresh et al., 1987, *J. Biol. Chem.,* 262:17703–17711.
Crowe et al., 1991, *Mechanisms and Specificity of HIV Entry into Host Cells,* 57–70.
Diegel et al., 1993, *AIDS Res. Human Retrovir.,* 9:465.
Fecondo et al., 1993, *AIDS Res. Human Retrovir.,* 9:733.
Fujita et al., 1992, *Jpn. J. Cancer Res.,* 83:1317–26.
Golding et al., 1992, *AIDS Res. Human Retrovir.,* 8:1593.
Gruber et al., 1991, *AIDS Res. Human Retrovir.,* 7:45.
Kreis et al., 1993, *Guidebook to the Extracellular Matrix and Adhesion Proteins,* p. 143.
Guo et al., 1993, *J. Immunol.,* 151:2225.
Hansen et al., 1991, *Scan J. Infect. Dis.,* 23:31–36.
Hart et al., 1991, *Cancer and Metastasis Rev.,* 10:115–128.
Hildreth et al., 1989, *Science,* 244:1075–1078.
Honn et al., 1992, *Exp. Cell Res.,* 201:23–32.
Humphries et al., 1986, *Science,* 233:467–70.
Johnson et al., 1989, *Proc. Natl. Acad. Sci. USA,* 86:641–644.
Kalter et al., 1991, *Immunol. Letters,* 30:219.
Kawaguchi et al., 1992, *Jpn. J. Cancer Res.,* 83:1304–1316.
Knudsen et al., 1988, *J. Cell. Physiol.,* 136:471–78.
Kramer et al., 1989, *Cancer Res.,* 49:393–402.
Kramer et al., 1991, *Cancer and Metastasis Rev.,* 10:49–59.
Meerloo et al., 1993, *J. Gen. Virol.,* 74:129.
Mortarini et al., 1992, *Cancer Res.,* 52:4499–4506.
Murata et al., 1992, *Jpn. J. Cancer Res.,* 83:1327–1333.
Nip et al., 1992, *J. Clin. Invest.,* 90:1406–1413.
Orentas et al., 1993, *AIDS Res. Human Retrovir.,* 9:1157.
Pantaleo et al., 1991, *J. Exp. Med.,* 173:511–514.
Pearce–Pratt et al., 1993, *Biology of Reproduction,* 48:431.
Roossien et al., 1989, *J. Cell Biol.,* 108:1979–83.
Saiki et al., 1990, *Jpn. J. Cancer Res.,* 81:660–67.
Saiki et al., 1990, *Jpn. J. Cancer Res.,* 81:668–75.
Saiki et al., 1990, *Jpn. J. Cancer Res.,* 81:1003–1011.
Smole et al., 1992, *FASEB J.,* 6:A1714.
Soszka et al., 1991, *Exp. Cell Res.,* 196:6–12.
Springer, 1990, *Nature,* 346:425.
Thieblemont et al., 1993, *Clin. Exp. Immunol.,* 92:106.
Ugen, 1988, *J. Natl. Cancer Inst.,* 80:1461.
Valentin et al., 1990, *J. Immunol.,* 144:934–937.
Van Muijen et al., 1991, *Int. J. Cancer,* 48:85–91.
Vermont–Desroches et al., 1991, *Molec. Immunol.,* 28:1095.
Vink et al., 1993, *Lab Invest.,* 68:192–203.
Vogel et al., 1993, *J. Cell Biol.,* 121:461.
Golding et al., 1992, *AIDS Res. Human Retrovir.,* 8:918.
Hermanowski–Vosatka et al., 1992, *Cell,* 68:341–52.
Pantaleo et al., 1991, *Eur. J. Immunol.,* 21:1771–74.
Patarroyo et al., 1990, *Immunol. Rev.,* pp. 67–108.
Bachelot et al., 1992, *Biochem J.,* 284:923–28.
Lawson et al., 1992, *Thrombosis Research,* 65:141–56.
Oelkers et al., 1992, *Arzneim.—Forsch/Drug Res.,* 42:136–39.
Sendl et al., 1992, *Atherosclerosis,* 94:79–95.
Sendl et al., 1992, *Planta Med.,* 58:1–7.
Siegel et al., 1991, *Z. Kardiologie 80 Supp. 7,* pp. 9–24.
Singh et al., 1992, *Mycologia,* 84:105–108.
Tadi et al., 1991, *Anticancer Research,* 11:2037–2042.
Acosta et al., 1994, *Am. J. Hosp. Pharm.,* 51:2251–2267.
Allen et al., 1995, *Medical Hypotheses,* 45:164–168.
Altieri et al., 1988, *Leukocyte Fibrinogen Receptor,* pp. 1893–1900.
Arthur et al., 1992, *Science,* 258:1935–1938.
Asselot–Chapel et al., 1993, HIV1 Infection of Macrophages Results in Modulation of Fibronectin and α5β1 Integrin Biosynthesis, IX International Conference on AIDS, PO–A12, p. 169.
Birdsall et al., 1994, *Journal of Leukocyte Biology,* 56:310–317.
Blobel et al., 1992, *Nature,* 356:248–252.
Bourinbaiar et al., 1993, *Acta. Virol.,* 37:21–28.
Bourinbaiar et al., 1994, *Cellular Immunology,* 155:230–236.
Bridges et al., 1994, *Antiviral Research,* 25:169–175.
Butera et al., 1992, *AIDS Res. and Human Retrovir.,* 8(6):991–995.

Butini et al., 1993, ICAM–1/2/3 Molecules Function as Counter–Receptors for LFA–1 in HIV–Mediated Syncytia Formation, *IX International Conference on AIDS*, PO–A14, p. 182.
Butini et al., 1994, *Eur. J. Immunol.*, 24:2191–2195.
Carlos et al., 1990, *Immunological Reviews*, 114:5–28.
Chehimi et al., 1993, *Journal of General Virology*, 74:1277–1285.
Clapham et al., 1993, *Phil. Trans. R. Soc. Lond. B*, 342:67–73.
Coller et al., 1989, *Circulation*, 80(6):1766–1774.
Collman et al., 1992, *Seminars in Virology*, 3:185–202.
Connor et al., 1994, *The New England J. of Medicine*, 331(18):1173–1180.
Cook et al., 1993, *Thrombosis and Haemostasis*, 70(5):838–847.
Denis, 1994, *The Journal of Immunology*, 153:2072–2081.
Douglas et al., 1994, *Journal of Reproductive Immunology*, 24:49–62.
Dullege et al., 1992, *VIII International Conference on AIDS*, PoB 3028.
Falanga et al., 1991, *Eur. J. Immunol.*, 21:2259–2263.
Faure et al., 1994, *Virus Research*, 34:1–13.
Ferguson et al., 1991, *Proc. Natl. Acad. Sci. USA*, 88:8072–8076.
Fletcher et al., 1993, *Journal of Clinical Pharmacy and Therapeutics*, 18:375–388.
Gehisen et al., 1992, *Clin. Exp. Metastasis*, 10:111–120.
Glander et al., 1993, *International Journal of Andrology*, 16:105–111.
Gonzalez–Scarano et al., 1992, *Seminars in Virology*, 3:225–234.
Gougeon et al., 1993, *Science*, 260:1269–1270.
Grau et al., 1991, *Eur. J. Immunol.*, 21:2265–2267.
Guo et al., 1995, *AIDS Res. and Human Retrovir.*, 11:1007–1013.
Hamilton et al., 1992, *The New England Journal of Medicine*, 326:437–443.
Hardan et al., 1993, *Int. J. Cancer*, 55, 1023–1028.
Harning et al., 1993, *Clin. Exp. Metastasis*, 11:337–342.
Haynes, 1993, *Science*, 260:1279–1286.
Huitinga et al., 1993, *Eur. J. Immunol.*, 23:709–715.
Isberg et al., 1994, *Trends in Microbiology*, 2(1):10–14.
Ishizuka et al., 1993, *Int. J. Immunopharmacol.*, 17(2):133–139.
Ito et al., 1992, *Journal of Virology*, 66(17):5999–6007.
Johnson, 1992, *AIDS Clinnical Review*, pp. 70–104.
Johnston, 1993, *Science*, 260:1286–1293.
Kavanaugh et al., 1994, *Arthritis & Rheumatism*, 37:992–999.
Kazazi et al., 1994, *Journal of General Virology*, 75:2795–2802.
Kolson et al., 1993, *AIDS Res. and Human Retrovir.*, 9(7):677–685.
Larson et al., 1990, *Immunological Reviews*, 114:181–216.
Levy, 1991, *Adv. Exp. Med. Biol.*, 300:1–15.
Li et al., 1995, *Science*, 268:429–431.
Locher et al., 1994, *Clin. Exp. Immunol.*, 98:115–122.
Mitsuya et al., 1991, *The FASEB Journal*, 5:2369–2381.
*MMWR* (Morbidity and Mortality Weekly Report, 43(16):285–287, 1994.
Mohan, 1993, *Drug Development Research*, 29:1–17.
Mould et al., 1991, *The Journal of Biological Chemistry*, 266(6):3579–3585.
Mousa et al., 1994, *Circulation*, 89(1):3–12.

Nemerow et al., 1994, *Trends in Cell Biology*, 4:53–55.
Ohta et al., 1994, *The EMBO Journal*, 13(9):2044–2055.
Palmer et al., 1993, *Clin, Exp. Immunol.*, 93:344–349.
Pantaleo et al., 1994, *Current Opinion in Immunology*, 6:600–604.
Paul, 1995, *Science*, 267:633–636.
Perez, 1994, *Antimicrobial Agents and Chemotherapy*, 38(2):337–339.
Phillips, 1994, *AIDS*, 8:719–731.
Reinhardt et al., 1993, *IX International Conference on AIDS*, PO–A14–0285, p. 182.
Reynolds–Kohler et al, 1991, *Mechanisms and Specificity of HIV Entry Into host Cells*, pp. 27–44.
Rossen et al., 1989, *Trans. Ass. Am. Physicians*, 102:117–130.
Sato et al., 1992, *Virology*, 186:712–724.
Scarborough et al., 1993, *The Journal of Biological Chemistry*, 268(2):1058–1065.
Schuitemaker et al., 1992, *Journal of Virology*, 66(3):1354–1360.
J.C., 1993, *Science*, 260:1256.
Shebuski et al., 1990, *Thrombosis and Haemostasis*, 64(4):576–581.
Sheu et al., 1994, *J. Lab. Clin. Med.*, 123(2):256–263.
Stent et al., 1994, *Journal of Leukocyte Biology*, 56:304–309.
Stevenson et al., 1992, *AIDS Res. and Human Retrovir.*, 8(2):107–117.
Tabata et al., 1994, *J. Immunol.*, 153:3256–3266.
Taichman et al., 1991, *Cell Regulation*, 2:347–355.
Tang et al., 1993, *Int. J. Cancer*, 54:338–347.
Tcheng et al., 1994, *Circulation*, 90(4):1757–1764.
Trikha et al., 1994, *Cancer Research*, 54:4993–4998.
Weeks et al., 1991, *J. Cell Biol.*, 114:847–853.
Aboulker et al., 1993, *The Lancet*, 341:889–890.
Yarchoan et al., 1992, *J. Enzyme Inhibition*, 6:99–111.
Yarchoan et al., 1991, *Blood*, 78(4):859–884.
Zahalka et al., 1993, *J. Immunol.*, 150:4446–4477.
Adler et al., 1992, *Biochemistry*, 31:1031–1039.
Adler et al., 1991, *Science*, 253:445–448.
Adler et al., 1993, *Biochemistry*, 32:282–289.
Au, et al., 1991, *Biochemical and Biophysical Research Communications*, 181(2):585–593.
Calvete et al., 1991, *Biochemistry*, 30:5225–5229.
Calvete, et al., 1992, *FEBS Letters*, 309(3):316–320.
Chang, et al., 1993, *Biochemical and Biophysical Research Communications*, 190(1):242–249.
Chao, et al., 1989, *Proc. Nat'l Acad. Sci. USA*, 86:8050–8054.
Chen, et al., 1991, *Biochemistry*, 30:11625–11636.
Cooke et al., 1991, *Eur. J. Biochem*, 202:323–328.
Dalvit et al., 1991, *Eur. J. Biochem*, 202:315–321.
Dennis et al., 1990, *Proc. Nat'l Acad. Sci. USA*, 87:2471–2475.
Dennis et al., 1993, *Proteins: Structure, Function and Genetics*, 15:312–321.
Fecondo, et al., 1993, *Aids Research and Human Retroviruses*, 9(8):733–740.
Gan, et al., 1988, *The Journal of Biological Chemistry*, 263(36):19827–19832.
Garsky et al., 1989, *Proc. Nat'l Acad. Sci. USA*, 86:4022–4026.
Glaser, 1995, *Genetic Engineering News*, 15(20):6–7.
Gould et al., 1990, *P.S.E.B.M.*, 195:168–171.
Hardan, I., et al., 1993, *Int. J. Cancer*, 55:1023.

Hite, et al., 1992, *Biochemistry,* 31:6203–6211.
Hite, et al., 1994, *Archives of Biochemistry and Biophysics,* 308(1):182–191.
Huang et al., 1991, *Biochimica et Biophysica Acta,* 1074:144–150.
Huang et al., 1991, *Biochimica et Biophysica Acta,* 1074:136–143.
Huang et al., 1991, *J. Biochem,* 109:328–334.
Huang et al., 1991, *Biochemical Pharmacology,* 42(6):1209–1219.
Huang et al., 1991, *Biochem J.,* 277:351–357.
Huang et al., 1987, *The Journal of Biological Chemistry,* 262(33):16157–16163.
Huang et al., 1989, *Biochemistry,* 28:661–666.
Humphries, M.J., et al., 1988, *J. Clin. Invest.,* p. 782.
Kini et al, 1990, *Toxicon,* 28(12):1387–1422.
Kini et al., 1992, *Toxicon,* 30(3):265–293.
Knudsen, et al., 1988, *Experimental Cell Research,* 179:42–49.
Mazur et al., 1991, *Eur. J. Biochem,* 202:1073–1082.
Musial, et al., 1990, *Circulation,* 82:261–273.
Neeper et al., 1990, *Nucleic Acids Research,* 18(14):4255.
Omori–Satoh, et al., 1986, *Toxicon,* 24(11–12):1045–1053.
Paine et al., 1992, *The Journal of Biological Chemistry,* 267(32):22869–22876.
Rucinski et al., 1990, *Biochimica et Biophysica Acta,* 1954:257–262.
Sato, et al., 1990, *Journal of Cell Biology,* 111:1713–1723.
Saudek et al., 1991, *Biochemistry,* 30:7369–7372.
Saudek et al., 1991, *Eur. J. Biochem,* 202:329–338.
Savage et al., 1990, *The Journal of Biological Chemistry,* 265(20):11766–11772.
Scarborough et al., 1993, *The Journal of Biological Chemistry,* 268(2):1066–1073.
Scarborough et al., 1991, *The Journal of Biological Chemistry,* 266(15):9359–9362.
Scarborough et al., 1993, *The Journal of Biological Chemistry,* 268(2):1058–1065.
Seymour et al., 1990, *The Journal of Biological Chemistry,* 265(17):10143–10147.
Shebuski et al., 1989, *The Journal of Biological Chemistry,* 264(36):21550–21556.
Shebuski et al., 1990, *Circulation,* 82:169–177.
Sheu et al., 1992, *Jpn. J. Cancer Res.,* 83:885–893.
Soszka et al., 1991, *Experimental Cell Research,* 196:6–12.
Takeya, et al., 1990, *The Journal of Biological Chemistry,* 265(27):16068–16073.
Takeya et al., 1992, *The Journal of Biological Chemistry,* 267(20):14109–14117.
Takeya et al., 1993, *J. Biochem,* 113:473–483.
Weber, et al., 1992, *Planta Med.,* 58:417–423.
Williams, et al., 1990, *Biochimica et Biophysica Acta,* 1039:81–89.
Yamakawa et al., 1991, *J. Biochem.,* 109:667–669.
Bone, 1991, *Annals of Internal Medicine,* 115:457–469.
Broaddus et al., 1994, *Journal of Immunology,* 152:2960–2967.
Feuerstein et al., 1987, *Am. Rev. Pharmacol. Toxicol.,* 27:301–313.
Fleckenstein et al., 1991, *Circulatory Shock,* 35:223–230.
Hub et al., 1996, *Chemoattractant Ligands And Their Receptors,* Chpt. 13, pp. 301–325.
Harlan et al., 1992, *Adhesion,* Chpt. 6, pp. 117–150.
Henderson, 1994, *Ann. Intern. Med.,* 121:684–697.
Hirvonen et al., 1989, *Z. Rechtsmed.,* 102:297–304.
Hsueh et al., 1986, *AJP,* 122(2):231–239.
Kellermann et al., 1989, *Klin Wochenschr,* 67:190–195.
Kishimoto et al., 1992, *Inflammation: Basic Principles And Clinical Correlates,* 2nd Ed., Chapter 20, pp. 353–406.
Lewis et al., 1990, *Mechanisms Of Disease,* 323(10):645–655.
Liu et al., 1992, *Adhesion,* Appendix, pp. 189–193.
Liu et al., 1992, *Adhesion,* Chapter 8, pp. 183–187.
Mosby, 1990, *Multiple Organ Failure: Patient Care and Prevention,* Chapter 10, pp. 235–263.
Mosby, 1990, *Multiple Organ Failure: Patient Care and Prevention,* Chapter 26, pp. 473–486.
Mukaida, et al., 1996, *Journal Of Leukocyte Biology,* 59:145–151.
Ogata et al., 1992, *Infection And Immunity,* 60(6):2432–2437.
Perbeck et al., 1980, *Acta Chir Scand,* 500(supp):91–94.
Samuelsson et al., 1987, *Science,* 237:1171–1176.
Shenep et al., 1984 *The Journal Of Infectious Diseases,* 150(3):380–388.
Simon et al., 1992, *Inflammation: Basic Principles and Clinical Correlates,* 2nd Ed., Chapt. 51, pp. 999–1016.
Spannagl et al., 1991, *Thrombosis Research,* 61:1–10.
Stevens et al., 1986, *J. Clin Invest.,* 77:1812–1816.
Svartholm et al., 1987, *Circulatory Shock,* 22:291–301.
Svartholm et al., 1987, *Circulatory Shock,* 22:173–183.
Terashita et al., 1987, *The Journal Of Pharmacology And Experimental Therapeutics,* 243(1):378–383.
Thörne et al., 1986, *Circulatory Shock,* 20:61–69.
Tracey, 1991, *Circulatory Shock,* 35:123–128.
VanOtteren et al., 1995, *The Journal Of Immunology,* 154:1900–1908.
Watanabe et al., 1995, *International Immunology,* 7(7):1037–1046.
Yeston et al., *Treatment Of Shock,* Chapter 4, pp. 59–80, 1985.
Bianchi et al., 1991, *Haematologica,* 76:383–388.
Bishop, 1991, *Cell,* 64:235–248.
Brodt et al., 1990, *Breast Cancer Research and Treatment,* 17:109–120.
Brodt, 1991, *Cancer and Metastasis Reviews,* 10:23–32.
Bukowski et al., 1991, *Journal of Immunotherapy,* 10:432–439.
Chambers et al., 1992, *Anticancer Research,* 12:43–48.
Chammas et al., 1991, *Tumor Biol.,* 12:309–320.
Dedhar, 1990, *BioEssays,* 12(12):583–590.
Felding–Habermann et al., 1992, *J. Clin. Invest.,* 89:2018–2022.
Giancotti et al., 1994, *Biochimica et Biophysica Acta,* 1198:47–64.
Heicappell et al., 1991, *World Journal of Urology,* 9:204–209.
Horst et al., 1991, *Leukemia,* 5(10):848–853.
Hermann et al., 1991, *Cancer Immunology Immunotherapy,* 34:111–114.
Hsiao et al., 1991, *J. Clin Invest.,* 87:811–820.
Ingber, 1992, *Seminars In Cancer Biology,* 3:57–63.
Inghirami et al., 1990, *Science,* 250:682–686.
Juliano et al., 1993, *Current Opinion In Cell Biology,* 5:812–816.
Kortlepel et al., 1993, *Leukemia,* 7(8):1174–1179.
Kramer et al., 1991, *Cell Regulation,* 2:805–817.
Krief et al., 1989, *Int. J. Cancer,* 43:658–664.
Mortarini et al., 1992, *Cancer Research,* 52:4499–4506.

Mueller et al., 1991, *Antibody, Immunoconjugates, and Radiopharmaceuticals,* 4(2):99–106.
Olive et al., 1991, *Journal Of Immunotherapy,* 10:412–417.
Pignatelli et al., 1991, *Journal Of Pathology,* 165:25–32.
Plantefaber et al., 1989, *Cell,* 56:281–290.
Postigo et al., 1991, *J. Exp. Med.,* 174:1313–1322.
Ramachandrula et al., 1992, *Journal Of Cell Science,* 101:859–871.
Ramos et al., 1991, *Invasion Metastasis,* 11:125–138.
Schreiner et al., 1991, *Cancer Research,* 51:1738–1740.
Van Waes et al., 1992, *Molecular Biology And Genetics,* 25(5):1117–1139.
Wake et al., 1995, *Blood,* 86(6):2257–2267.
Witjes et al., 1995, *Carcinogenesis,* 16(11)2825–2832.
Zutter et al., 1990, *American Journal Of Pathology,* 137(4):863–870.
Belman et al., *Chem. Abstracts,* 112:91227 (1990).
Delaha et al., *Chem. Abstracts,* 102, 218177j, (1985).
Delaha et al., 1985, *Antimicrob. Agents Chemother.,* 27(4):485–6.
Demers et al., *Chem. Abstracts,* 116:128198 (1992).
Douvas et al., 1991, *Proc. Nat'l Acad. Sci USA,* 88:6328–6332.
Lichtenstein et al., *Chem. Abstracts,* 104, 45756h, (1986).
Meng, et al., 1990, *Nutr. Cancer,* 14(3–4):207–17.
Merck Index, No. 185 (1989).
Mohr, *Chem. Abstracts,* 108, 54653g, (1988).
Mohr, 1987, *Gordian,* 87(10):195–6 and English translation.
Nakagawa et al., 1989, *Chem. Abstracts,* 111:146760e.
Nakagawa et al., 1989, *Phytotherapy Res.,* 3:50–53.
Nakata, 1973, *Nippon Eiseigaku Zasshi,* 27(6):538–43 and English translation.

Nishikawa et al., *Chem. Abstracts,* 74:30034j (1971).
Perez et al., *Chem. Abstracts,* 120, 182454c, (1994).
Qian et al., *Chem. Abstracts,* 106, 13095s, (1987).
Qian et al., 1986, *Contraception,* 34(3):295–302.
Sabata et al., *Chem. Abstracts,* 508135 (1986).
Saeed et al., *Chem. Abstracts,* 107:400435 (1987).
Shah et al., *Chem. Abstracts,* 113, 204565z, (1990).
Shah et al., 1990, *Fitoterapia,* 61(2):121–6.
Soma et al., *Chem. Abstracts,* 116, 76349e, (1992).
Sumiyoshi et al., 1990, *Cancer Res.,* 50(16):5084–7.
Tsai et al., 1985, *Planta Medica,* pp. 460–461.
Wagner et al., *Chem. Abstracts,* 107:489878 (1987).
Wakunaga Seiyaku KK, Derwent WIPDS, Abstract Corresponding to JP 62 129224 (1987).
Agarwal, 1996, *Med. Res. Rev.,* 16:111–124.
Bai et al., 1994, *J. Virol.,* 68:5925.
Carey et al., 1992, *Monogr. Natl. Cancer Inst.,* 75.
Falcioni et al., 1994, *Exp. Cell Res.,* 210:113.
Freeman et al., 1995, *J. Agric. Food Chem.,* 43:2332.
Hemler, in Guidebook to the Extracellular Matrix, pp. 143–145 (Kreis and Vale eds. 1993).
Holmes et al., 1994, *AIDS Res. Hum. Retrovir.,* 10:S53.
Majda et al., 1994, *Exp. Cell Res.,* 210:46.
Pigott and Power, The Adhesion Molecule Facts Book, pp. 9–12 (1993).
Tadi et al 116CA: 1875862 1991.
Sumiyoshi et al 113CA: 126061R 1990.
Meng et al 115CA: 439500 1991.
Dausch et al 113CA: 184048C 1990.
Nakata et al 79CA: 111680X 1973.

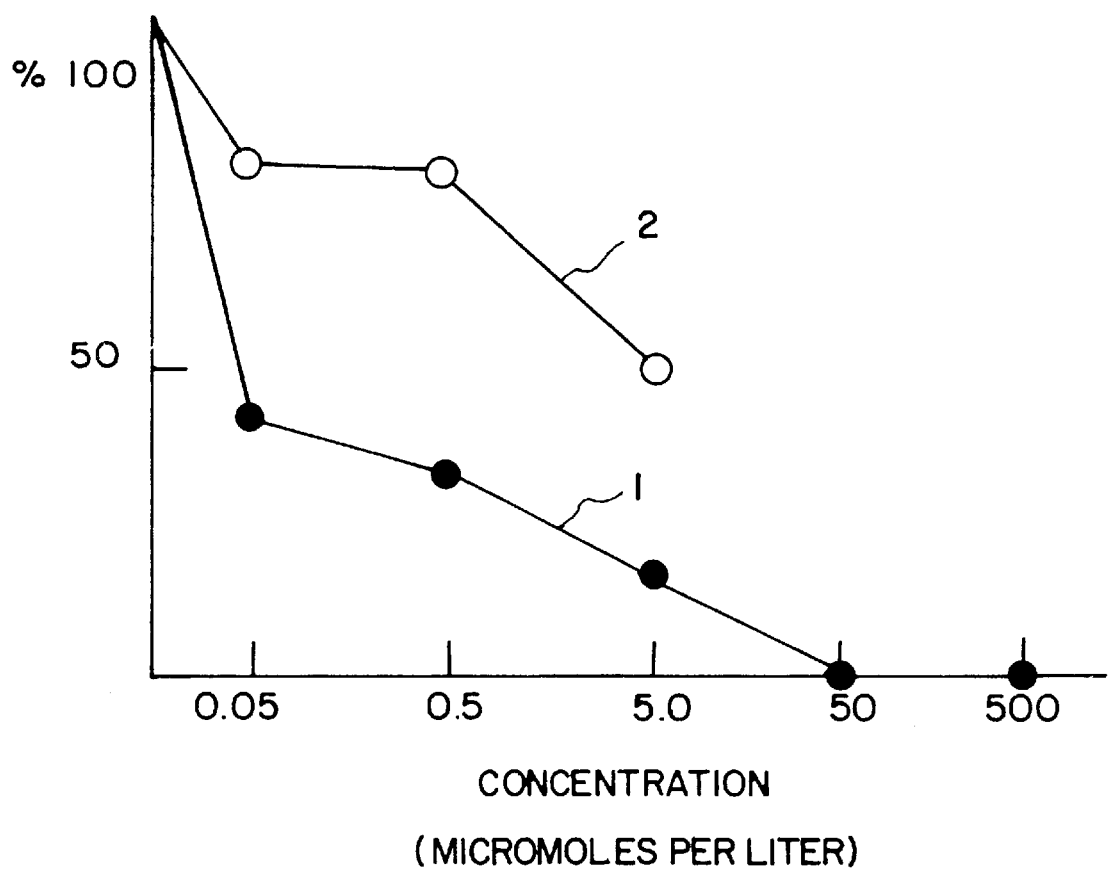

METHODS OF USING AJOENE FOR THE TREATMENT OF TUMORS

This application is a division of application number 07/906,850, filed Jun. 30, 1992, now abandoned.

BACKGROUND OF THE INVENTION

Ajoene is 4,5,9-trithiadodeca-1,6,11-triene-9-oxide, having a structural formula as follows:

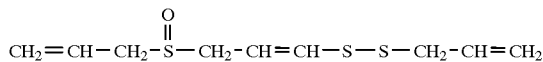

Ajoene, and a precursor thereof, can be isolated from extracts of garlic (*Allium sativum*). As the garlic is crushed, alliin in the garlic comes into contact with allinase in the cell wall to form allicin. Then, in the presence of a polar molecule such as a lower alcohol or even water, allicin forms Ajoene.

Ajoene has been previously shown to inhibit platelet aggregation by inactivating allosterically the platelet integrin, GP IIb/IIIa (Apitz-Castro R. et al.: *Biophys. Res. Commun.*, 1986, 141:145). This inhibition of integrins by Ajoene is reversible.

Also, integrin-mediated formation of cell-to-cell contacts has been shown to typically be a prerequisite for membrane fusion (Hildreth, J. E. K. and Orentas, R. J., Science, 1989, 244:1075).

DESCRIPTION OF THE INVENTION

By this invention, safe and effective doses of Ajoene may inhibit the progression of an HIV infection in a patient. Specifically, stereoisomer mixtures of Ajoene may be used, although pure (E) and (Z) stereoisomer forms may also be used.

One of the characteristics of an HIV infection so inhibited is the formation of HIV-induced syncytia, in which HIV target cells such as lymphocytes and monocytes clump together to form giant, polynuclear cells in HIV-infected patients. This inhibiting effect would require a sufficient dose to provide a concentration of Ajoene of at least 50 nanomoles per liter of blood plasma in the patient, and preferably at least 200 nanomoles of Ajoene per liter of plasma. Transfer of genetic material between cells will, therefore, also be inhibited by Ajoene.

Additionally, it appears that Ajoene inhibits the growth of HIV-infected cells, HIV, and other viruses, also inhibits the incorporation of HIV into CD4-negative cells. For this purpose, Ajoene is preferably administered in sufficient dose to provide a concentration of at least 5,000 nanomoles per liter of patient's blood plasma, although lesser concentrations may also be effective.

Additionally, the growth of tumors such as T-lymphomas and the development of melanoma metastasis may be inhibited by administering to the patient, human or animal, a safe and effective dosage of Ajoene, preferably to provide a concentration of Ajoene to the patient of at least 50 micromoles per liter of the patient's blood plasma, or at least in the blood adjacent the tumor, for example in cases of regional perfusion where steps are taken to minimize the concentration of Ajoene elsewhere in the body except at the tumor site.

Ajoene serves as an agent that inhibits the aggregation of blood cells, such as platelets and neutrophils. Ajoene may, therefore, exhibit benefit as an agent for the treatment of pathologies derived from aggregation of these cells, including, in part, the effects of shock. In cases of shock, platelets and neutrophils aggregate in the blood vessels of the lungs, which may be a primary cause of death in that oxygen transfer through the lungs is degraded, leading to death. Ajoene may thus counteract at least part of the effects of shock, for example in sepsis, anaphylaxis, or in blood loss. The inhibiting effect of Ajoene in this use would typically be the result of a dose to provide a concentration of Ajoene of at least 10 micromoles per liter of the patient's blood plasma.

Ajoene can also be administered in effective dosage to suppress many inflammation processes, for example, those inflammation processes that occur in the lungs as a consequence of severe shock. Inflammation is a typical pathological process (i.e., either inherent in or associated with a variety of distinct diseases and illnesses), defensive in nature, but potentially dangerous if uncontrolled. There are several indices of inflammation at the "whole body" level: e.g., hemodynamic disorders (e.g., hyperemia and edema), pain, temperature increment, and functional lesion. At the cellular level, inflammation is characterized by leukocyte emigration into tissues (where they phagocytose bacteria, viruses, or other invaders) and platelet aggregation (to localize the infection), which emigration and aggregation may also have a destructive effect on tissue. At the molecular level, inflammation is characterized by activation of at least three plasma defense systems (complement, kinin, and coagulation cascades), and by synthesis of cytokines and eicosanoids.

When inflammation is generalized, as in the case of shock, the various indices of inflammation may become disseminated and occur throughout the entire organismn.

Without wishing to be limited to any particular mechanism of operation of Ajoene, it is believed that the beneficial effects of Ajoene are achieved because Ajoene is an inactivating agent for several integrin receptors of cells. Thus, it is believed that other inactivating agents for cell integrin receptors may exhibit similar benefits as Ajoene, particularly with respect to the suppression of adhesion events mediating HIV spread in the body (e.g., adhesion-induced HIV budding, infection of $CD4^-$ cells, cell-to-cell transmission of infection by cell fusion, infection by virus having adhesion molecules captured from host cells, syncytia formation in the central nervous system).

Work by others has shown that HIV-1 Tat protein stimulates the growth of AIDS-Kaposils sarcoma (AIDS-KS) cells by interacting with the integrins $α_5β_1$ and $α_vβ_3$. Ajoene should, therefore, be effective in treating Kaposi's sarcoma in view of its ability to inactivate integrins.

The above disclosure and the examples below are for illustrative purposes only, and are not intended to limit the invention of this application, which is as defined in the claims below.

EXAMPLE 1

Ajoene as an Inhibitor of HIV-Mediated Syncytia Formation

Intact H9 cells and chronically infected H9:RF cells (a cloned population of H9 cells harboring HIV genome) were maintained in suspension in RPMI-1640 medium supplemented with 10% (v/v) heat-inactivated fetal calf serum, 50 micrograms/ml gentamycin and 2 mM L-glutamine. Syncytium formation was assessed by co-cultivation of H9 cells and H9:RF cells (2:1) for 16 hrs with various concentrations of Ajoene in 96-well flat-bottomed plates, $3\times10^5$ cells per well. By the end of the incubation period syncytia were counted. $IC_{50}$ for Ajoene was calculated by plotting relative amount of syncytia (percent of the syncytia formed in the absence of the compound) against Ajoene concentration. If not specified otherwise, Ajoene was used as a 1:1 mixture of (E)- and(Z)-stereoisomers.

Specifically, Ajoene inhibited fusion of intact H9 cells with HIV-infected H9:RF cells ($IC_{50}$ of 50 nanomoles per liter Ajoene concentration at 16 hrs incubation).

EXAMPLE 2

Ajoene as an Inactivator of Several Distinct Integrin Receptors

Platelet aggregation was measured turbidimetrically on a standard platelet aggregometer equipped with a recorder. Samples of platelet-rich plasma (PRP) were standardized with respect to the cell density ($3\times10^8$ per ml); maximal light transmission (LT) was calibrated with platelet-poor plasma (PPP). Aliquots of PRP (0.25 ml in glass cuvettes) were stirred in the cell of the device (1000 rpm, 37° C.) with Ajoene (0–100 micromoles per liter final concentration) for 1 min., followed by addition of the stimuli. LT increments were traced for 5 min. Maximal rate of aggregation was derived from the slope of each curve; $IC_{50}$ for Ajoene was determined by a method such as that described in Vrzheshch PV, Tatarintsev AV, Yershov DE et al.: Cell Response Kinetics: the Phenomenon of Supercooperativity in Aggregation of Human Platelets. *Dokl. Akad. Nauk SSSR*, 1989, 307:477 (in Russian). Neutrophil aggregation was assayed as described above for the platelet system, with some modifications. Freshly isolated neutrophils were finally suspended in a buffer (120 mM NaCl, 4 mM KCl, 10 mM dextrose, 2 mM $CaCl_2.2H_2O$, 2 mM $MgCl_2.6H_2O$, and 20 mM Tris; pH 7.4) to the final density of $10^7$ cells per ml. Aliquots of neutrophil suspension (0.25 ml in siliconized glass cuvettes; $10^7$ cells per ml) were stirred in the cell of the aggregometer with 5 micrograms per ml cytochalasin B (1000 rpm, 37° C.) for 1 min. Ajoene (0–50 micromoles per liter) and N-formyl-L-methionyl-L-leucyl-L-phenylalanine ($10^{-7}M$) were then introduced into the suspension sequentially, with an interval of 1 min. Maximum LT (100%) was calibrated with the same buffer. H9 and Jurkat cells were cultured as described above in Example 1.

Ajoene inhibited platelet aggregation in PRP with an $IC_{50}$ of about 50 micromoles per liter. Ajoene blocked N-formyl-L-methionyl-L-leucyl-L-phenylalanine-stimulated neutrophil aggregation ($IC_{100}$ of about 10 micromoles per liter) and caused rapid deaggregation when added to aggregated neutrophils. The clusters normally formed by H9 and Jurkat cells in culture were disrupted by Ajoene with an $IC_{50}$ of about 50 nanomoles per liter.

Though the requirement of integrins for contact interactions in either of these systems has long been established, the molecular mechanisms are clearly nonidentical. It is known that in platelets the relevant integrin is GP IIb/IIIa. Neutrophils form contacts via interaction of LFA-1 and/or Mac-1 with their surface counterstructures, while cohesion of T-cells is supported by LFA-1 and by fibronectin-binding VLA integrins. Hence, Ajoene is apparently capable of inactivating integrin receptors of at least three distinct subfamilies ($\beta_1$, $\beta_2$ and $\beta_3$) One probable mechanism is that the compound either binds to a region which is highly conserved within the members of the integrin superfamily, or somehow alters the microenvironment, thereby inactivating the whole receptor. At the cellular level this inactivation appears as a severe (but controllable) deficiency in the respective cell-specific integrins, i.e., inability for aggregation (platelets, neutrophils), disintegration of cell clusters (intact H9 and Jurkat cells), failure to fuse (HIV-infected cells; Example 1).

EXAMPLE 3

Ajoene As An Inhibitor of HIV Replication

LAV-BRU 1 isolate of HIV-1 and RF isolate of HIV-1 were propagated in CEM and H9 cells, respectively. A 20-ml log-phase culture containing $7\times10^5$ cells per ml was incubated at 37° C. for 24 hrs. Cultures with less than 10% trypan blue stained cells were used as a source of virus. To harvest HIV particles, producer cells were pelleted by centrifugation (400 g, 5 min) and the supernatant containing HIV-1 particles was filtered through a 0.45 micrometer Millipore filter, aliquoted and stored at −80° C. The titer of HIV-1 ranged from $1\times10^5$ to $2\times10^5$ $CCID_{50}$ (50% cell culture infective dose). To determine whether Ajoene could also influence HIV replication, CEM13 and H9 cells were inoculated with appropriate amounts of HIV (LAV-BRU 1 and RF, respectively), to give an m.o.i. (multeity of infection) of 0.1 in either experimental setting. Ajoene (or its vehicle) was added to $10^7$ infected cells resuspended in the growth medium and the cells were plated in 96-well flat-bottomed plates. After 72 hrs the bulk of HIV antigens was measured by solid phase immunoassay as described in Zhdanov VM, Karamov EV, Arakelov SA, et al.: An Enzyme Immunoassay for Detection of Antigen and Antibody to Human Immunodeficiency Virus and the Use Thereof For serological Survey of Different Population Groups. Vop Virusol 1988, N3:292 (in Russian). In a series of separate experiments Ajoene was introduced into plated cell cultures stepwise, i.e. in aliquots of 50 nanomoles per liter concentration per 12 hrs of incubation, the first addition coinciding with the moment of inoculation.

Replication of HIV-1 (RF) in H9 cells was inhibited with an $IC_{50}$ of 25 micromoles per liter (m.o.i. 0.1; 72 hrs of incubation). Assessment of HIV-1 (LAV-BRU 1) replication in CEM13 cells under the same experimental conditions revealed a more pronounced anti-viral activity ($IC_{50}$ of about 5 micromoles per liter concentration). A considerable increase in the latter became evident when the concentration of the compound was increased stepwise (50 nanomoles per liter concentration per 12 hrs of incubation; CEM13—LAV-BRU 1 system; inhibition by 30%; total concentration 0.25 micromoles per liter; m.o.i. 0.1; 72 hrs of incubation).

EXAMPLE 4

Ajoene as a Potential Anti-Shock Agent

Neutrophil aggregation within the lung microvasculature is known to be a key event in the development of the so-called adult respiratory distress syndrome (ARDS), the main cause of death in patients suffering shock. Also, administration of neutrophil-aggregating agents (such as phorbol-myristate-acetate, complement anaphylotoxins or N-formyl-L-methionyl-L-phenylalanine, calcium ionophore A23187, arachidonic acid, platelet-activating factor) to laboratory animals also results in the development of ARDS. Some inhibitors of neutrophil aggregation, such as antagonists of the platelet-activating factor, have been shown to prevent lethality in experimental septic shock, Toyofoku T. et al.: Effects of ONO-6340, a Platelet-Activating Factor Antagonist, on Endotoxin Shock in Unanesthetized Sheep. Prostaglandins, 1986, 31:271). It is believed that beneficial effects of glucocorticoids in various shock states are largely due to their ability for inhibition of neutrophil aggregation (Hammerschmidt, et al., J. Clin. Invest. 1979, 63:798; Cronstein, B. N. et al., Proc. Natl. Acad. Sci. USA, 1992, 89: 9991–99).

The antiaggregatory activity of Ajoene disclosed in Example 2 above is sufficiently high to expect that Ajoene will be effective both for the prevention and treatment of various shock states by suppressing such aggregation.

EXAMPLE 5

Ajoene as an Antineoplastic Agent

Leukemic (CEM, MT2, MT4) and lymphoid (H9, Jurkat) T-cells were cultured as described above (Example 1) with various concentrations of Ajoene, and the toxic effects were assessed by the cytocidal activity ($LD_{100}$).

For T-lymphoid tumor cells, $LD_{100}$ was achieved after 72 hrs of culturing in a media of about 50 micromoles of Ajoene per liter.

For Leukemia T cells $LD_{100}$ was achieved after 72 hrs of culturing in a media of about 500 micromoles of Ajoene per liter.

EXAMPLE 6

Ajoene as an Antimetastatic Agent

Male C57BL/6 mice were used as experimental animals. Murine platelet aggregation was measured as described above (Example 3). To evaluate the effect of the compound on experimental metastasis, a suspension of $10^5$ melanoma B16 cells was pretreated for 30 min with Ajoene or its vehicle, and the suspension (including Ajoene or its vehicle) was injected intravenously into mice. The mice were sacrificed 3 weeks post-injection, and their lungs subjected to microscopic examination. To evaluate the effect on tumor cell implantation, mice were inoculated subcutaneously with $10^6$ B16 cells (pretreated for 15 min with Ajoene or its vehicle) in their pretreatment medium, and the volume of the tumors formed was measured 14 and 21 days after the injection.

Ajoene inhibited ADP-induced aggregation of PRP with an $IC_{100}$ of 200 micromoles per liter. Pretreatment of B16 cells with Ajoene (200 micromoles per liter) rendered them incapable of colonizing lungs. Subcutaneous implantation was prevented by exposing the cells to 2500 micromolar concentration of Ajoene. At 2.5 micromolar concentration of the compound, the volume of melanomas was reduced by one-half.

EXAMPLE 7

Integrin-Inactivating Properties of Ajoene are not Stereospecific

Synthetic stereoisomers of Ajoene exhibited equal antiaggregatory activity ($IC_{50}$ of about 50 micromolar concentration of Ajoene for platelets, $IC_{100}$ of about 10 micromolar concentration of Ajoene for neutrophils).

BRIEF DESCRIPTION OF THE DRAWING

Referring to FIG. 1, the effect of Ajoene on syncytia formation and HIV replication is shown.

For curve 1, the effect of Ajoene on the infusion of cultured, intact H9 cells with HIV infected H9:RF cells is disclosed. For this curve, the vertical graph axis pertains to the maximum amount of syncytia formed in the absence of Ajoene (100 percent), while the points on line 1 represent percentages of such an amount of syncytia formed in the presence of varying concentrations of Ajoene (micromoles per liter). The $IC_{50}$ of syncytia formation was found at a concentration of 0.045 micromole of Ajoene per liter. Essentially no syncytia were found at a concentration of 50 micromoles of Ajoene per liter.

Referring to curve 2, the antiviral activity of Ajoene is shown, as assessed by the inhibition of HIV-1 (Lav—BRU 1) replication in cultured CEM13 cells. Here, the vertical axis represents the percentage of HIV antigens detected by solid phase immunoassay (previously mentioned) in the absence of Ajoene.

The $IC_{50}$ was achieved under these conditions at about a 5 micromole concentration of Ajoene.

Thus, Ajoene exhibits significant potential as an effective anti-HIV drug to reduce or eliminate the course of the disease while exhibiting relatively low toxic effects. Ajoene is also effective against many tumor cells and their metastasis. In addition, Ajoene exhibits significant potential as an effective drug to block cell aggregation, for example in various shock states. Finally, Ajoene may be used to treat inflammation.

To treat one of these conditions, an effective amount of Ajoene is administered. Effective dosage forms, modes of administration and dosage amounts, may be determined empirically, and making such determinations is within the skill of the art. It is understood by those skilled in the art that the dosage amount will vary with the severity of the condition, the route of administration, the rate of excretion, the duration of the treatment, the identity of any other drugs being administered, the age, size and species of the animal, and like factors well known in the medical and veterinary arts. In general, a suitable daily dose of Ajoene will be that amount of the compound which is the lowest dose effective to produce a therapeutic effect. However, the total daily dosage will be determined by an attending physician or veterinarian within the scope of sound medical judgment. If desired, the effective daily dose of Ajoene may be administered as two, three, four, five, six or more sub-doses, administered separately at appropriate intervals throughout the day.

Ajoene may be administered in any desired and effective manner: as a pharmaceutical preparation for oral ingestion, or for parenteral or other administration in any appropriate manner such as intraperitoneal, subcutaneous, topical, inhalation, intrapulmonary, rectal, vaginal, sublingual, intramuscular, intravenous, intraarterial, intrathecal, or intralymphatic. For instance, the topical application of Ajoene to mucous membranes can be used to prevent HIV infection of mucosal cells, an important route of HIV transmission. In addition, intralymphatic administration of Ajoene may be advantageous in preventing the spread of HIV within the body. Further, Ajoene may be administered in conjunction with other anti-HIV drugs, other chemotherapy agents for tumor or metastasis treatment, and other anti-shock or anti-inflammation drugs or treatments. The Ajoene may be encapsulated or otherwise protected against gastric or other secretions, if desired.

The above has been offered for illustrative purposes only, and is not intended to limit the scope of the invention of this application, which is as described in the claims below.

I claim:

1. A method of inhibiting integrin-mediated tumor metastasis in an animal in need thereof comprising administering to the animal an amount of ajoene effective to inhibit integrins and metastasis of the tumor.

2. The method of claim 1 wherein the ajoene is administered in sufficient amount to provide a concentration of at least 50 micromoles per liter of blood plasma.

3. The method of claim 2 wherein the ajoene is administered in sufficient amount to provide a concentration of at least 200 micromoles per liter of blood plasma.

4. The method of claim 1 or wherein the agent is administered intralymphatically.

5. A method of treating an integrin-mediated cancer in an animal in need thereof comprising administering to the animal an amount of ajoene effective to inhibit integrins and the cancer.

6. The method of claim 5 wherein the cancer is a T-cell cancer.

7. The method of claim 5 wherein the cancer is a melanoma.

8. The method of claim 5, 6 or 7 wherein the ajoene is administered in sufficient amount to provide a concentration of at least 50 micromoles per liter of blood plasma.

9. The method of claim 8 wherein the ajoene is administered in sufficient amount to provide a concentration of at least 2500 micromoles per liter of blood plasma.

10. The method of claim 5, 6 or 7 wherein the ajoene is administered intralymphatically.

11. A method of treating Kaposi's sarcoma in an HIV-infected patient comprising administering to the patient a therapeutically effective amount of ajoene.

* * * * *

UNITED STATES PATENT AND TRADEMARK OFFICE
CERTIFICATE OF CORRECTION

PATENT NO. : 5,932,621
DATED : August 3, 1999
INVENTOR(S) : Tatarintsev

It is certified that error appears in the above-identified patent and that said Letters Patent is hereby corrected as shown below:

In Claim 4, delete "agent" and insert –ajoene– therefor.

Signed and Sealed this

Seventh Day of December, 1999

*Attest:*

Q. TODD DICKINSON

*Attesting Officer*    *Acting Commissioner of Patents and Trademarks*